(12) United States Patent  (10) Patent No.: US 9,572,373 B2
Chen  (45) Date of Patent: Feb. 21, 2017

(54) ELECTRONIC CIGARETTE

(71) Applicant: SHENZHEN SMOORE TECHNOLOGY LIMITED, Shenzhen (CN)

(72) Inventor: Zhiping Chen, Shenzhen (CN)

(73) Assignee: Shenzhen Smoore Technology Limited, Shenzhen (CN)

( * ) Notice: Subject to any disclaimer, the term of this patent is extended or adjusted under 35 U.S.C. 154(b) by 497 days.

(21) Appl. No.: 14/144,772

(22) Filed: Dec. 31, 2013

(65) Prior Publication Data

US 2015/0090280 A1    Apr. 2, 2015

(30) Foreign Application Priority Data

Sep. 29, 2013 (CN) .......................... 2013 1 0459545

(51) Int. Cl.
A24F 47/00 (2006.01)
(52) U.S. Cl.
CPC .................................. A24F 47/008 (2013.01)
(58) Field of Classification Search
CPC ........ A24F 47/00; A24F 47/008; A61M 15/06
USPC ........................................................ 131/329
See application file for complete search history.

(56) References Cited

U.S. PATENT DOCUMENTS

| 2011/0126848 | A1* | 6/2011 | Zuber | A24F 47/008 |
| | | | | 131/329 |
| 2011/0277760 | A1* | 11/2011 | Terry | A24F 47/008 |
| | | | | 128/203.12 |
| 2012/0279512 | A1* | 11/2012 | Hon | A24F 47/008 |
| | | | | 131/329 |
| 2015/0007835 | A1* | 1/2015 | Liu | A24F 47/008 |
| | | | | 131/329 |

FOREIGN PATENT DOCUMENTS

CN    WO 2010091593 A1 *  8/2010  ........... A24F 47/008

* cited by examiner

*Primary Examiner* — Joseph S Del Sole
*Assistant Examiner* — Mohamed K Ahmed Ali
(74) *Attorney, Agent, or Firm* — Coats & Bennett, P.L.L.C.

(57) ABSTRACT

An electronic cigarette is provided, which includes: a housing having a chimney formed therein; a liquid reservoir for storing liquid in the housing; and an atomizer assembly received in the housing. The atomizer assembly includes a heating tube capable of absorbing liquid. The heating tube defines a plurality of micropores on a wall thereof; an inner surface of the heating tube is in contact with the air in the chimney.

17 Claims, 7 Drawing Sheets

ELECTRONIC CIGARETTE

FIELD OF THE INVENTION

The present disclosure relates to an electronic cigarette.

BACKGROUND OF THE INVENTION

The electronic cigarette is also known as a virtual cigarette or an electronic atomizer. As a replacement for cigarettes, the electronic cigarette is usually used for smoking cessation. The appearance and taste of the electronic cigarette are similar to that of the conventional cigarette, while it does not contain tar, suspended particles and other harmful ingredients such as the conventional cigarette.

The electronic cigarette is mainly composed of an atomizer and a battery assembly. The atomizer is the core device of the electronic cigarette to generate atomizing gas; the quality and taste of the smoke are dependent on the atomization effect. A conventional heating element of the atomizer can only heat and atomize the liquid located close to the heating wire. As such the atomization effect of the liquid located away from the heating wire is poor. Or even if the liquid can be atomized, the atomized particles are relatively large due to the low atomization temperature.

SUMMARY OF THE DISCLOSURE

This section provides a general summary of the disclosure, and is not a comprehensive disclosure of its full scope or all of its features.

The present disclosure is directed to an electronic cigarette having a better atomization effect.

An electronic cigarette includes a housing having a chimney formed therein; a liquid reservoir received in the housing; and an atomizer assembly received in the housing, the atomizer assembly includes a heating tube capable of absorbing liquid, the heating tube defines a plurality of micropores on a wall thereof, an inner surface of the heating tube is in contact with an air in the chimney.

The housing has a receiving cavity for receiving various internal components of the electronic cigarette, such as the atomizer assembly and the liquid reservoir.

In one embodiment, the liquid reservoir is a component mainly used for storing liquid. In one embodiment, the liquid reservoir is a liquid container located in the housing but is independent from the housing. Alternatively, it can also be a container with an opening formed by surrounding of a part of the wall of the housing. Or it can be made of fibers, blankets, temperature resistant and non-toxic sponges, and other materials with great capacity of absorbing liquid, such that the liquid can be filled or stored in the liquid reservoir. Further, the shape of the liquid reservoir is adapted to that of the housing, such as rectangular or cylinder and so on. In addition, the liquid reservoir can be configured in any position of the receiving cavity, such as in the center or close to one side of the receiving cavity, as long as the chimney is not blocked by the liquid reservoir.

In one embodiment, the chimney is used as an air passage. The chimney can be located in the center of the housing, or close to one side of the housing. When the chimney is located close to the side of the housing, at least partial wall of the chimney is integrally formed with the wall of the liquid reservoir. The atomized particles generated by the atomizer assembly can pass through the chimney and go out of the housing.

The liquid can be atomized by the atomizer assembly to form atomizing gas for consumers to inhale. The atomizer assembly includes at least a heating tube capable of absorbing liquid.

In one embodiment, the heating tube defines a plurality of micropores on a wall thereof. A density of the micropores on the heating tube is 1200 to 4900 micropores per square centimeter. Accordingly, the surface area of the heating tube is enlarged, and the storing capability of the heating tube is improved. The liquid is uniformly distributed on the heating tube, and the liquid is capable of passing through the wall of the heating tube.

Alternatively, the heating tube can be configured with other structures.

For example, in one embodiment, the heating tube is a mixed woven tube composed of flexible heating strips and heating resistant fibers. The heating tube has a plurality of through micropores on itself. Further, the flexible heating strips are metal wires or conductive fibers, the heating resistant fibers are glass fibers or carbon fibers.

In an alternative embodiment, the heating tube includes a tubular substrate and a heating film covered on the substrate. Further, the heating film is a positive temperature coefficient (PTC) film or a conductive heating coating layer. The substrate is made of microporous material. The PTC film is a membranous heating wire coated on the surface of the substrate. Accordingly, the whole heating tube can heat when the PTC film or conductive heating coating layer is heating, and the liquid absorbed by the heating tube can be atomized when the heating tube is passively heated.

In an alternative embodiment, the heating tube is made of foamed metal, foamed graphite or porous ceramic. And the liquid absorbed by the heating tube can be atomized when the heating tube is heated by itself.

At least a partial surface of the heating tube is in contact with the air in the chimney. It means that at least a partial surface of the heating plate is exposed to the air in the chimney. Accordingly, the liquid can be atomized by the heating tube and then diffused to the air in the chimney, and the flowing air brings it out of the chimney.

Compared to the prior art, the foregoing technical solution has the following advantages:

1. Since the heating tube has a plurality of micropores, the liquid stored in the liquid reservoir can be absorbed by the heating tube by capillarity. Then the liquid is free to crawl on the heating tube, thus the liquid can be uniformly distributed on the heating tube and uniformly heated to form uniformly atomized particles. Besides, a heating area of the heating tube is enlarged due to the micropores, the contact area between the heating tube and the liquid is also enlarged, the speed of the atomization is accelerated. The liquid can pass through the wall of the heating tube due to the plurality of micropores, such that the purpose of absorbing by one side of the heating tube and atomizing by the other side is achieved.

2. Furthermore, the heating area of the heating tube is much larger due to the tubular shape of the heating tube. Since a proper amount of the liquid is heated, the atomization effect is improved, and since a proper amount of smoke is generated, the taste is great. In addition, the fabrication process of the heating tube is relatively simple, and there is no need to twine a heating wire around a fixed axis, the assembly operation is then simplified.

In one embodiment, the liquid reservoir surrounds at least a partial outer wall of the heating tube; the air in the chimney is capable of passing through the heating tube.

In one embodiment, the liquid reservoir surrounds at least a partial outer wall of the heating tube, which can be regarded as the inner surface of the liquid reservoir and the outer surface of the heating tube are bonded to each other. The liquid stored in the liquid reservoir can be directly absorbed by the heating tube, the flow of the liquid can be adjusted by adjusting the contact area between the inner surface of the liquid reservoir and the outer surface of the heating tube, the phenomenon of too much or too little liquid absorbed to the heating tube is avoided, and the atomization is not affected. An air gap may be defined between the inner surface of the liquid reservoir and the outer surface of the heating tube, and the liquid reservoir is only in contact with partial heating tube. A liquid conductor may be provided between the liquid reservoir and the heating tube. The liquid stored in the liquid reservoir can be transferred to the heating tube by the liquid conductor. The flow of the liquid can also be adjusted by adjusting the number or the cross-sectional area of the liquid conductor. In addition, the liquid reservoir can reduce the heat transferred from the heating tube to the housing besides transferring the liquid stored in the liquid reservoir to the heating tube. The loss of the heat from the heating tube to the housing is reduced. And the efficiency of the heat of the heating tube is improved. And the risk that the housing is thermal deformed or even harm to consumers can be avoided. Moreover, the liquid reservoir can also be used as a supporter for the heating tube, accordingly, the inner structure of the electronic cigarette is simplified, and the number of the mounting components in the housing is reduced, the space for the air circulation is enlarged such that the consumers can easily inhale the smoke.

Furthermore, the air in the chimney can pass through the heating tube, thereby the liquid atomized by the heating tube can go out by passing through the heating tube and enter the chimney. Moreover, the space for the air circulation in the housing is further enlarged such that the consumers can easily inhale the smoke.

Furthermore, the heating tube surrounds at least partial outer wall of the liquid reservoir; the air in the chimney is capable of blowing the outer surface of the heating tube.

The heating tube surrounds at least a partial outer wall of the liquid reservoir, which can be regarded as the inner surface of the heating tube and the outer surface of the liquid reservoir are bonded to each other. The liquid stored in the liquid reservoir can be directly absorbed by the heating tube, the flow of the liquid can be adjusted by adjusting the contact area between the inner surface of the liquid reservoir and the outer surface of the heating tube, thereby the phenomenon of too much or too little liquid absorbed to the heating tube is avoided, and the atomization effect is not affected. Alternatively, an air space is defined between the inner surface of the heating tube and the outer surface of the liquid reservoir, and the liquid reservoir is only in contact with partial heating tube. Or a liquid conductor is provided between the liquid reservoir and the heating tube. The liquid stored in the liquid reservoir can be transferred to the heating tube by the liquid conductor. The flow of the liquid can be adjusted by adjusting the number or the cross-sectional area of the liquid conductor.

Further, the air in the chimney is capable of blowing the outer surface of the heating tube, when the electronic cigarette is in use; the flowing air in the housing is capable of contacting with the outer surface of the heating tube and bringing out the atomized liquid on the surface of the heating tube.

Further, the electronic cigarette includes a liquid conductor, an end of the liquid conductor is connected to the liquid reservoir, and the other is extended inside the tube of the heating tube.

In one embodiment, the liquid conductor is made from fibers, sponges, and other material with great capacity of absorbing liquid; the liquid conductor can also be made of fine pipette. The liquid can be transported by capillary action, the phenomenon that the heating tube is directly in contact with the liquid reservoir is avoided, and the loss of a large number of the heat transferring to the liquid reservoir is reduced. Accordingly, the efficiency of the heat is greatly enhanced, and the risk that the liquid reservoir is accelerated aged because the liquid reservoir is heated for the long time by the heating tube is avoided, and the risk that the powder generated by the liquid reservoir affects the quality of the smoke is avoided, moreover, the risk of the damage of the liquid reservoir caused by the heating tube is also avoided.

Further, the heating tube defines a groove extending along an axial direction on an inner wall or an outer wall thereof. The contact area between the liquid reservoir and the heating tube can be adjusted by adjusting the groove, and the groove can form an assisted chimney to enhance the gas flux.

The electronic cigarette can be a replacement for cigarettes for smoking cessation due to its features and benefits.

Further areas of applicability will become apparent from the description provided herein. The description and specific examples in this summary are intended for purpose of illustration only and are not intended to limit the scope of the present disclosure.

BRIEF DESCRIPTION OF THE DRAWINGS

The components in the drawings are not necessarily drawn to scale, the emphasis instead being placed upon clearly illustrating the principles of the present disclosure. Moreover, in the drawings, like reference numerals designate corresponding parts throughout the views.

DETAILED DESCRIPTION OF THE EMBODIMENTS

Illustrative embodiments of the disclosure are below. The following explanation provides specific details for a thorough understanding of and enabling description for these embodiments. One skilled in the art will understand that the disclosure may be practiced without such details. In other instances, well-known structures and functions have not been shown or described in detail to avoid unnecessarily obscuring the description of the embodiments.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list.

Example One

Figure 1:
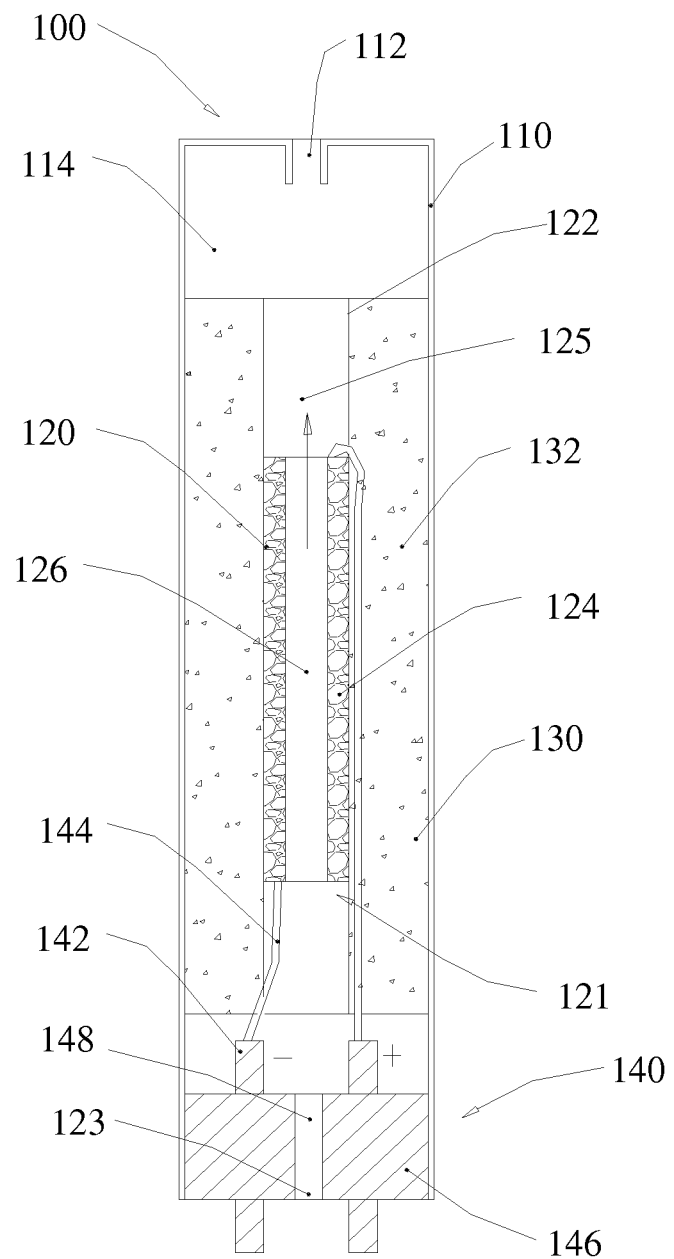
FIG. 1 is a cross-sectional view of an electronic cigarette according to a first embodiment.
Figure 2:
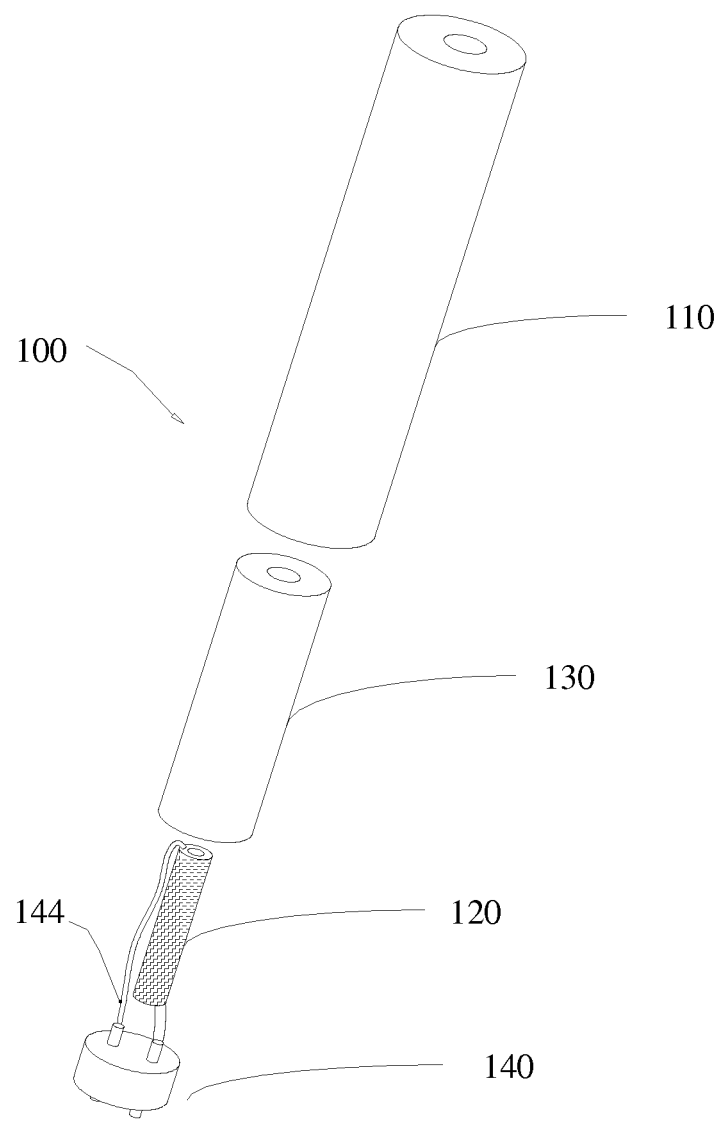
FIG. 2 is an exploded perspective view of the electronic cigarette shown in FIG. 1.

Referring to FIG. 1 and FIG. 2, a first embodiment of an electronic cigarette 100 includes a housing 110, a liquid reservoir 130, a power supply assembly 140, and an atomizer assembly 121. The liquid reservoir 130, the power supply assembly 140, and the atomizer assembly 121 are received in the housing 110. The power supply assembly 140 is used to supply power to the atomizer assembly 121.

The housing 110 is made of plastic, which is approximately shaped as a hollow cylinder. The housing 110 has a cavity for receiving various internal components of the electronic cigarette 100. In alternative embodiments, the housing 110 may have a shape of a rectangular cylinder, oval cylinder and so on. The housing 110 defines an air outlet 112 on an end thereof and an air intake 123 on the other end thereof. The housing 110 forms a chimney 122 therein to connect the air outlet 112 and the air intake 123. In one embodiment, the housing 110 is provided with a filter nozzle (not shown) close to the end of the air outlet 112 to filter nicotine and other chemical substances in the smoke.

In the illustrated embodiment, the liquid reservoir 130 is made of temperature resistance and non-toxic sponge, thus the liquid can be absorbed and stored in the liquid reservoir 130. The liquid reservoir 130 has a receiving channel 125 extending along an axial direction, partial inner wall of the receiving channel 125 surrounds the outer wall of the heating tube 120, and the receiving channel 125 forms part of the chimney 122. In addition, the liquid reservoir 130 and the air outlet 112 define a buffer space 114, and the filter nozzle is located in the buffer space 114.

The atomizer assembly 121 includes a heating tube 120. The heating tube 120 has a channel 126, which forms part of the chimney 122, such that the air in the chimney 122 is in contact with thus the inner surface of the heating tube 120. The wall of the heating tube 120 defines a plurality of micropores 124 thereof. Partial inner surface of the receiving channel 125 is bonded to the outer surface of the heating tube 120. Accordingly, the liquid stored in the liquid reservoir 130 can be directly absorbed by the heating tube 120 by capillary action, and the liquid is free to crawl on the heating tube 120 and pass through the micropores 124 on the wall of the heating tube 120. The liquid can be uniformly heated to form uniformly atomized particles. Besides, the heating area of the heating tube 120 is enlarged due to the micropores 124, and the contact area between the heating tube 120 and the liquid is also enlarged, the speed of the atomization is accelerated The heating tube 120 has a much larger heating area. A proper amount of the liquid is heated, and a uniform particles and a suitable amount of smoke are generated, thus the taste is great. In addition, the fabrication process of the heating tube 120 is relatively simple, and there is no need to twine a heating wire around a fixed axis, thereby the assembly operation is simplified. The flow of the liquid can be adjusted by adjusting the contact area between the inner surface of the liquid reservoir 130 and the outer surface of the heating tube 120; the risk that the atomization effect is affected by too much or too less liquid absorbed by the heating tube 120 is avoided.

In addition, the liquid reservoir 130 surrounds at least partial outer surface of the heating tube 120, such that the heat transferred from the heating tube 120 to the housing 110 is reduced. The loss of the heat of the heating tube 120 is reduced and the efficiency of the heat of the heating tube 120 is improved. Moreover, the risk that the housing is thermal deformed or even harm to consumers is avoided. The liquid reservoir 130 can also be used as a supporter for the heating tube 120 to simplify the inner structure of the electronic cigarette 100. What is much important is that the amount of the mounting components in the housing 110 is reduced, the space for the air circulation is enlarged, such that the consumers can easily inhale the smoke.

Furthermore, the air in the chimney 122 can pass through the tube 126 of the heating tube 120. The liquid can pass through micropores 124 on the wall of the heating tube 120 to the inner surface, and the atomized liquid can be bought out by the air in the tube 126 and enter the chimney 122, the space for the air circulation in the housing 110 is further enlarged, such that the consumers can easily inhale the smoke.

Figure 3:
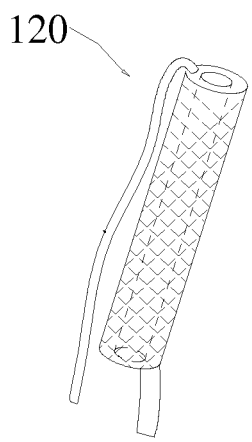
FIG. 3 is a perspective view of the heating tube shown in FIG. 2.
Figure 4:
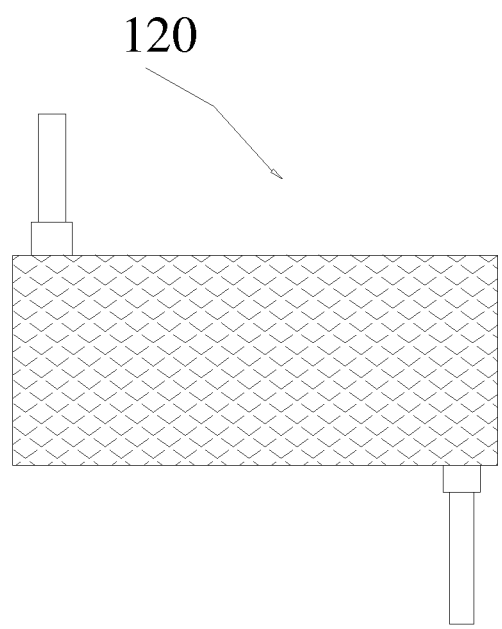
FIG. 4 is a front view of the heating tube shown in FIG. 3 in an expanded state.

The structure of the heating tube 120 is shown in FIG. 3. In the illustrated embodiment, the heating tube 120 is a mixed woven tube composed of flexible heating strips and heating resistant fibers. The mixed woven tube has a microporous structure itself, the impurities in the liquid can pass through the micropores to be removed from the mixed woven tube, or it can be absorbed by the heating resistant fibers of the mixed woven tube, thereby the impurities are not likely to remain on the flexible heating strips of the mixed woven tube to affect the heating effect. The flexible heating strips may be metal wires or conductive fibers and the like, as long as they can be woven. The heating resistant fibers can be glass fibers or carbon fibers with temperature resistance. The flexible heating strips are mixed with the heating resistant fibers to form a tubular heating surface with greater superficial area. The absorption capacity of the heating resistant fibers is great, the absorption area is also great, and the flexible heating strips are sufficiently in contact with heating resistant fibers, such that the atomization effect is great. FIG. 4 is a front view of the heating tube 120 in an expanded state, the mixed woven tube is grid-like. The fabrication process of the mixed woven tube is simple and with strong variability. Compared to the heating tube of the conventional electronic cigarette, the heating tube 120 can be automated produced, and the production difficulty is reduced. The process parameters such as electric resistance are also easier to be controlled.

Referring to FIG. 1 and FIG. 2 again, the power supply assembly 140 is electrically connected to the heating tube 120 to supply power to the heating tube 120. In the illustrated embodiment, the power supply assembly 140 includes an electrode 142, a wire 144, an electrode support 146, and battery (not shown). The electrode 142 is connected to the heating tube 120 by the wire 144. The electrode 142 is inserted into the electrode support 146, the electrode support 146 defines an air hole 148 for air circulation. Alternatively, the electrode support 146 can be omitted.

The assembly process of the electronic cigarette 100 is described as follows: first of all, the liquid reservoir 130 is fixed in the cavity of the housing 110, and the heating tube 120 is connected to the electrode 142 of the power supply assembly 140 by the wire 144, then the electrode 142 is inserted into the electrode support 146, finally, the housing 110 is sleeved to the electrode support 146 and the process is finished. It should be understood that the assembly sequence can be adjusted as needed.

In use, as the arrows shown in the FIG. 1, when the user inhales the electronic cigarette 100 on the end of the air outlet 112, the airflow enters the electronic cigarette 100 from the air intake 123, then passes through the air hole 148 of the electrode support 146, and carries the atomized liquid to the chimney 122, and finally enters the mouth of the user by passing through the air outlet 112.

Example Two

Figure 5:
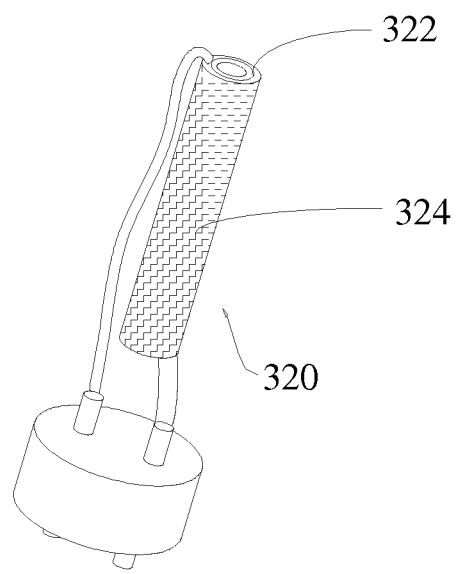
FIG. 5 is a perspective view of the heating tube according to a second embodiment.

Referring to FIG. 5, the heating tube 320 of a second embodiment is similar to the heating tube 120 of the first embodiment, the difference is that: in the illustrated embodiment, the heating tube 320 includes a substrate 322 and a heating film 324. The substrate 322 is made of a material with an internal microporous structure, and a density of the micropores is 2000 to 3000 per square centimeter on the heating tube 320. The substrate 322 has a hollow tubular shape. The heating film 324 is coated on the substrate 322. In the illustrated embodiment, the heating film 324 is formed by coating a conductive heating coating layer on the substrate 322. Further, the conductive heating coating is coated on both the inner surface and the outer surface of the substrate 322 to increase the heating area. The conductive heating coating may be made of carbon black, aluminum, or aluminum dihydrogen phosphate. In alternative embodiments, the conductive heating coating may contain metal fibers and carbon fibers painting, plastics and the conductive carbon particles painting, or metal powders painting and the other conductive particles painting. There is no need to twine a heating wire around the fixed axis to form the heating tube 320, thereby the assembly operation is simplified and the cost is down. The material of the heating tube 320 is more environmentally friendly, and the resistance is relatively stable.

Example Three

Figure 6:
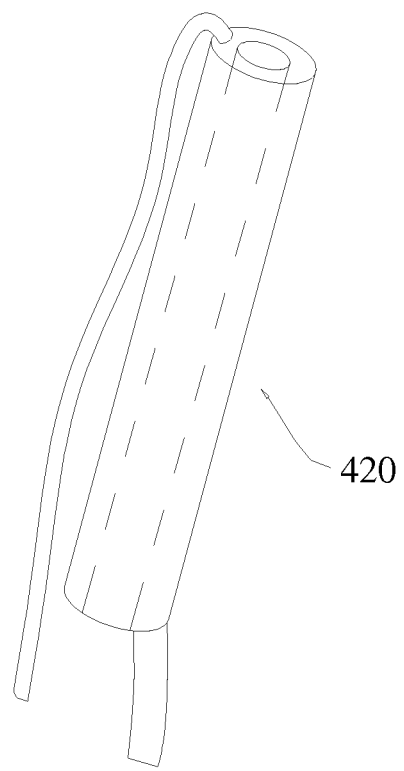
FIG. 6 is a perspective view of the heating tube according to a third embodiment.

Referring to FIG. 6, the heating tube 420 of a third embodiment is similar to the heating tube 120 of the first embodiment, the difference is that: in the illustrated embodiment, the heating tube 420 is made of foamed metal, foamed graphite or porous ceramic. The heating tube 420 has a plurality of internal micropores formed by extruding or firing, thus the heating tube 420 can be heated by itself. The foamed metal, foamed graphite or porous ceramic possesses the functions of heating and absorbing liquid, the absorbed liquid is atomized when heating. Moreover, the foamed metal, foamed graphite or porous ceramic possesses the properties of high electrical conductivity and thermal conductivity, and also has the characteristics of large specific surface area, completely through holes, high porosity, lightweight, and easy processing. Besides, the foamed metal, foamed graphite or porous ceramic has a certain strength and rigidity, the fixed device such as the fixed axis is omitted, thereby the structure and assembly operation are simplified. Moreover, the heating tube 420 can be fabricated by using a standard mold, thus the resistance and size can be easy adjusted. In the illustrated embodiment, the heating tube 420 is made of foamed nickel-chromium.

Example Four

Figure 7:
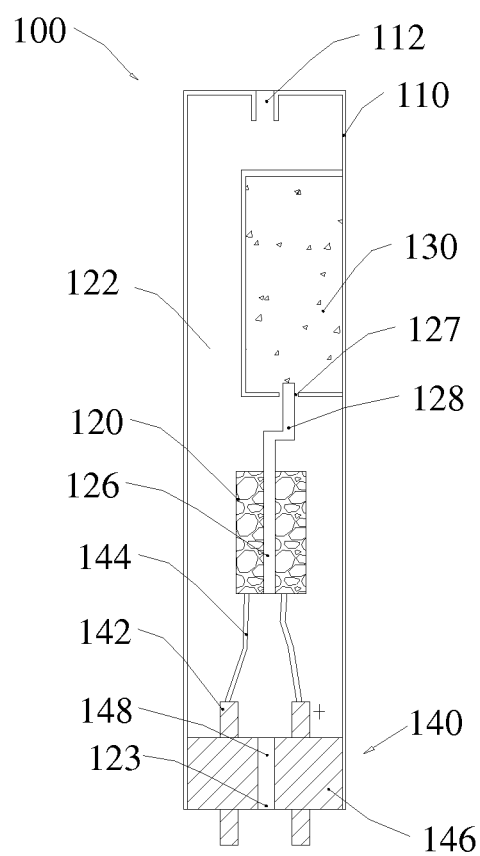
FIG. 7 is a cross-sectional view of the electronic cigarette according to a fourth embodiment.

Referring to FIG. 7, the electronic cigarette 100 of a fourth embodiment is similar to that of the first embodiment, the difference is that: the tube 126 of the heating tube 120 is not a part of the chimney 122, while the chimney 122 is formed by a wall of the heating tube 120 and an inner wall of the housing 110. The outer surface of the heating tube 120 is in contact with the air in the chimney 122, thereby the air in the chimney 122 is capable of blowing the outer surface of the heating tube 120. The liquid reservoir 130 is fixed to the housing 110. In the illustrated embodiment, the liquid reservoir 130 is a sealed container surrounded by partial wall of the housing 110 and used for store the liquid. The liquid reservoir 130 is approximately cylindrical. In the illustrated embodiment, a cross-sectional area of the liquid reservoir 130 is smaller than that of the housing 110, and a wall of the liquid reservoir 130 and an inner wall of the housing 110 cooperatively forms part of the chimney 122. The liquid reservoir 130 defines a liquid outlet 127 at an end thereof.

A liquid conductor 128 is provided between the liquid reservoir 130 and the heating tube 120. The liquid conductor 128 is made of sponge with great capacity for absorbing liquid. One end of the liquid conductor 128 is connected to the liquid outlet 127 of the liquid reservoir 130, and the other end is extended inside the tube 126 of the heating tube 120. The liquid stored in the liquid reservoir 130 can be transported by capillary action, and the phenomenon that the heating tube 120 is directly in contact with the liquid reservoir 130 can be avoided, and a large number of heat transferring to the liquid reservoir 130 is reduced. Accordingly, the efficiency of the heat is greatly increased, and the risk that the liquid reservoir 130 is accelerated aged because the liquid reservoir 130 is heated for the long time by the heating tube 120 can be avoided, the risk that the powder generated by the liquid reservoir 130 affects the quality of the smoke can also be avoided. Moreover, the risk of the damage of the liquid reservoir 130 caused by the heating tube 120 can be avoided. The flowing air in the housing 110 can be in contact with the outer surface of the heating tube 120 and bring out the atomized liquid on the outer surface of the heating tube 120.

Example Five

Figure 8:
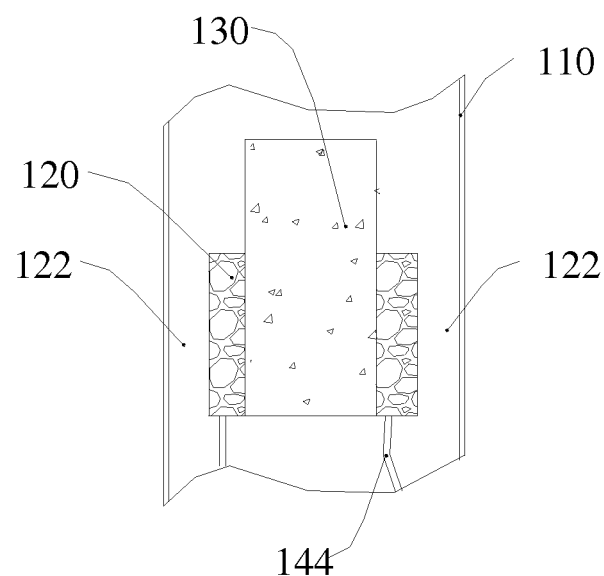
FIG. 8 is a partial, cross-sectional view of the electronic cigarette according to a fifth embodiment.

Referring to FIG. 8, the electronic cigarette 100 of a fifth embodiment is similar to that of the fourth embodiment, the difference is that: the heating tube 120 surrounds partial outer surface of the liquid reservoir 130. The chimney 122 is located outside of the heating tube 120, thereby the outer surface of the heating tube 120 is in contact with the air in the chimney 122, the air in the chimney 122 is capable of blowing the outer surface of the heating tube 120. It is a better structure to solve the problem caused by large doses of atomization of the liquid.

Example Six

Figure 9:
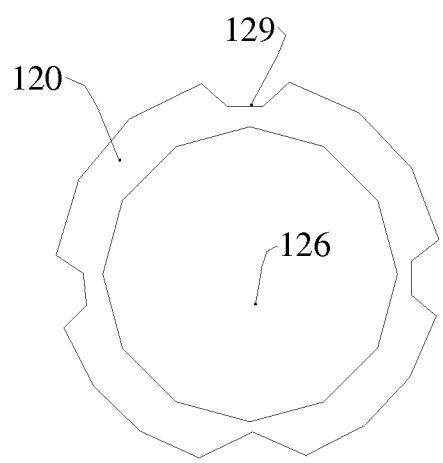
FIG. 9 is a bottom plan view of the heating tube according to a sixth embodiment.

Referring to FIG. 9, in the illustrated embodiment, the heating tube 120 further defines a groove 129 extending along an axial direction on an outer wall thereof. Alternatively, the heating tube 120 can define a groove 129 extending along an axial direction on an inner wall thereof. The contact area between the liquid reservoir 130 and the heating tube 120 can be adjusted by adjusting the groove 129, and the groove 129 can also form an assisted chimney to enhance the gas flux.

Although the subject matter has been described in language specific to structural features, it is to be understood that the subject matter defined in the appended claims is not necessarily limited to the specific features described above. Rather, the specific features described above are disclosed as example forms of implementing the claims. Numerous modifications and alternative arrangements can be devised without departing from the spirit and scope of the described technology.

What is claimed is:

1. An electronic cigarette, comprising:
   a housing having a chimney formed therein with the chimney defining a longitudinal axis;
   a liquid reservoir received in the housing; and
   an atomizer assembly received in the housing,
   wherein the atomizer assembly comprises a heating tube capable of absorbing liquid, the heating tube defines a plurality of micropores on a wall thereof, an inner surface of the heating tube is in contact with air in the chimney; the liquid reservoir and the heating tube overlap along the longitudinal axis of the chimney with a side of the liquid reservoir being bonded to a side of the heating tube so the liquid in the liquid reservoir can be directly absorbed by the heating tube;
   a surface of the heating tube opposite from the liquid reservoir being exposed across an entirety of the overlap with the liquid reservoir;
   wherein the heating tube is a mixed woven tube composed of flexible heating strips and heating resistant fibers;
   wherein the heating tube defines a groove extending axially on an outer surface thereof for adjusting a contact area between the liquid reservoir and the heating tube.

2. The electronic cigarette according to claim 1, wherein the liquid reservoir at least partially surrounds an outer wall of the heating tube, the air in the chimney is capable of passing through the heating tube.

3. The electronic cigarette according to claim 1, wherein the heating tube at least partially surrounds the liquid reservoir, the air in the chimney is capable of blowing across an outer surface of the heating tube.

4. The electronic cigarette according to claim 1, further comprising a liquid conductor, wherein an end of the liquid conductor is connected to the liquid reservoir, and the other end of the liquid conductor is extended inside the heating tube.

5. The electronic cigarette according to claim 4, wherein the liquid conductor is made of fibers or sponges.

6. The electronic cigarette according to claim 1, wherein the flexible heating strips are metal wires or conductive fibers, the heating resistant fibers are selected from the group consisting of glass fibers, and carbon fibers.

7. The electronic cigarette according to claim 1, wherein the heating tube comprises a tubular substrate and a heating film covered on a surface of the substrate.

8. The electronic cigarette according to claim 7, wherein the heating film is a PTC film or a conductive heating coating layer.

9. The electronic cigarette according to claim 1, wherein the heating tube is made of foamed metal, foamed graphite or porous ceramic.

10. The electronic cigarette according to claim 1, wherein the liquid reservoir is a container with an opening, the liquid reservoir formed partially by a wall of the housing.

11. The electronic cigarette according to claim 1, wherein the chimney is located in a center of the housing.

12. The electronic cigarette according to claim 1, wherein the chimney is located close to a side of the housing; and at least a portion of a wall of the chimney is integrally formed with a wall of the liquid reservoir.

13. The electronic cigarette according to claim 1, wherein a density of the micropores on the heating tube is 1200 to 4900 micropores per square centimeter.

14. The electronic cigarette according to claim 1, wherein the liquid reservoir defines a receiving channel extending along an axial direction, and an inner wall of the receiving channel surrounds the outer wall of the heating tube.

15. The electronic cigarette according to claim 1, wherein a cross-sectional area of the liquid reservoir is smaller than a cross-sectional area of the housing; and the chimney is formed by a wall of the liquid reservoir and a wall of the housing.

16. The electronic cigarette according to claim 1, wherein an inner surface of the liquid reservoir and an outer surface of the heating tube are bonded to each other.

17. The electronic cigarette according to claim 1, wherein an inner surface of the heating tube and an outer surface of the liquid reservoir are bonded to each other.

* * * * *